(12) United States Patent
Nick et al.

(10) Patent No.: US 9,248,142 B2
(45) Date of Patent: Feb. 2, 2016

(54) NON-HORMONAL FEMALE CONTRACEPTIVE

(75) Inventors: Harry S. Nick, Gainesville, FL (US); Kimberly J. Aiken, Alachua, FL (US); Sarah J. Barilovits, Charlotte, NC (US); Justin S. Bickford, Gainesville, FL (US); Dawn E. Beachy, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 131 days.

(21) Appl. No.: 13/882,263

(22) PCT Filed: Oct. 28, 2011

(86) PCT No.: PCT/US2011/058369
§ 371 (c)(1),
(2), (4) Date: Aug. 13, 2013

(87) PCT Pub. No.: WO2012/058581
PCT Pub. Date: May 3, 2012

(65) Prior Publication Data
US 2013/0315974 A1    Nov. 28, 2013

Related U.S. Application Data

(60) Provisional application No. 61/407,510, filed on Oct. 28, 2010.

(51) Int. Cl.
*A61K 31/70*    (2006.01)
*A61K 31/7004*    (2006.01)
*A61K 45/06*    (2006.01)
*G01N 33/50*    (2006.01)

(52) U.S. Cl.
CPC ............. *A61K 31/7004* (2013.01); *A61K 31/70* (2013.01); *A61K 45/06* (2013.01); *G01N 33/5044* (2013.01)

(58) Field of Classification Search
CPC .... A61K 45/06; A61K 31/70; A61K 31/7004
See application file for complete search history.

(56) References Cited

U.S. PATENT DOCUMENTS 6,110,471 A    8/2000  Conti et al.
2005/0153922 A1    7/2005  Edelmann et al.

FOREIGN PATENT DOCUMENTS

WO    2005007687 A1    1/2005

OTHER PUBLICATIONS

Williams et al., "The role of glucose in supporting motility and capacitation in human spermatozoa", Journal of Andrology, vol. 22, No. 4, Jul./Aug. 2001.*

(Continued)

*Primary Examiner* — Ernst V Arnold
*Assistant Examiner* — Kyung Sook Chang
(74) *Attorney, Agent, or Firm* — Timothy H. Van Dyke; Beusse, Wolter, Sanks & Maire, PLLC

(57) ABSTRACT

Disclosed herein are compositions and methods for controlling fertility of a female subject. Particularly exemplified are compositions comprising sugar derivatives, such as 2-deoxyglucose, D-mannoheptulose; and/or 5-thio-D-glucose. Also disclosed herein are methods of preserving ova supply in a female subject that involves administering glucose derivatives. The composition typically includes a glucose derivative that affects Foxo3a expression.

9 Claims, 5 Drawing Sheets

(56) References Cited

OTHER PUBLICATIONS

Zhong et al., "2-deoxyglucose induces Akt phosphorylation via a mechanism independent of LKB1/AMP-activated protein kinase signaling activation or glycolysis inhibition", Mol Cancer Ther 2008: 7(4), Apr. 2008.*

Lobl, T.J. et al., "Antifertility Activities of 5-THIO-D-Glucose in Mice and Rats", Contraception, Feb. 1978, vol. 17, No. 2, pp. 123-130 (abstract only).

International Search Report; PCT/US2011/058369, (Jun. 15, 2012).

* cited by examiner

NON-HORMONAL FEMALE CONTRACEPTIVE

CROSS-REFERENCE TO RELATED APPLICATIONS

This application is related to U.S. Provisional Application No. 61/407,510; filed Oct. 28, 2010, to which priority is claimed under 35 USC 119, and which is incorporated herein in its entirety.

FIELD OF THE INVENTION

The present invention relates to compositions and methods for controlling fertility, prolonging oocyte supply, and delaying the onset of menopause in a female subject.

BACKGROUND OF THE INVENTION

Currently there are two main types of female contraception, both of which are hormone dependent. These hormonal contraceptive methods act by preventing fertilization of the ovum by sperm cells or preventing implantation of the embryo.

Hormonal contraception has various significant negative effects on female patients. One negative effect associated with both oral and injectable hormonal contraceptives is a decrease in bone mineral density. A study demonstrated that women using depot medroxyprogesterone acetate (injection hormonal contraceptive) for 24 months experienced on average a 5.7% loss in bone mineral density with 3.2% of the loss occurring between months 12 and 24. Users of desogestrel pills (oral hormonal contraceptive) experienced a 2.6% loss in bone mineral density after 24 months. Berenson, et al. Effects of Hormonal Contraception on Bone Mineral Density After 24 Months of Use. *The American College of Obstetricians and Gynecologists*. 2004; 103:899-906.

Additional negative effects associated with hormonal contraception include changes in body composition including weight gain. The hormonal effects of oral contraception include an increase in mean body weight, mainly caused by an increase in both upper and lower body fat, with no change in lean body mass. See Rickenlund, et al. Effects of Oral Contraceptives on Body composition and Physical Performance in Female Athletes. *The Journal of Clinical Endocrinology & Metabolism*. 2004; 89(9):4364-4370. Sex steroids have also been shown to interfere with appetite and metabolic functions. Estradiol reduces appetite in animals, whereas high dose progestins are appetite stimulating. Id.

Sex steroid hormones, including hormonal contraceptives also play a role in disease predisposition for many genital tract infections. Their effects are variable and influence susceptibility, severity of symptoms, risk of re-infection, and persistence or risk of disease prolongation. See Brabin, L. Interactions of the Female Hormonal environment, Susceptibility to Viral Infections, and Disease Progression. *AIDS Patient Care and STDs*. 2002; 16(5):211-221.

In light of the foregoing negative impacts of hormonal contraceptives, the inventors have discovered a need for a contraceptive which prevents or inhibits ovulation and thus ultimately fertilization without administering hormones to female patients.

DETAILED DESCRIPTION OF THE INVENTION

Figure 1:
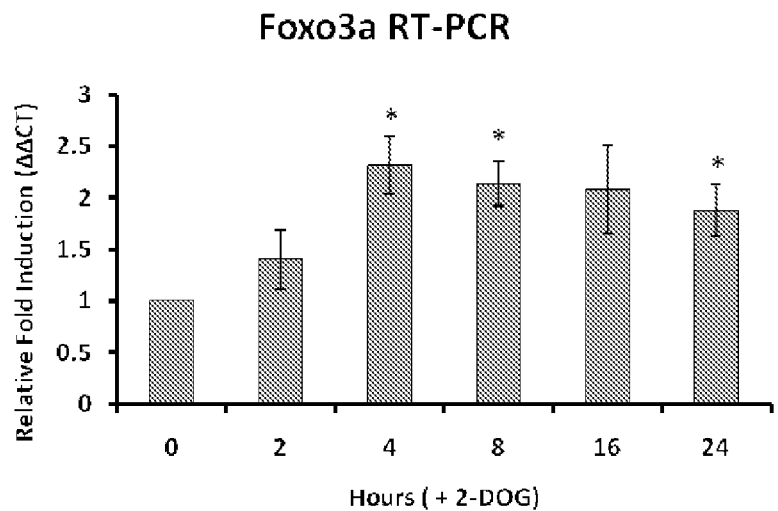
FIG. 1 demonstrates 2-DG treatment of human cells induces Foxo3a approximately 2.5 fold by 4 h.

The inventors have developed a non-hormonal female contraceptive that provides a contraceptive having a low cost, that is self-administrable, and has minimal side effects. In particular, it has been discovered that glucose analogs elevate the production of an ovarian master regulatory factor known to be the "brake" in oocytes that prevents their activation during follicle development and maturation. This analog acts to block ovulation and in turn provide a unique/novel, non-hormonal approach to contraception. Embodiments of the present invention use an unconventional approach to contraception by taking advantage of intra-cellular mechanisms using non-hormonal drug agents that are simple derivatives of glucose.

These glucose analog compounds are low cost and in some embodiments are orally administrable, thus providing a discrete and acceptable alternative to hormone-based approaches. Although more than one route can be used to administer a particular compound, a particular route can provide a more immediate and more effective reaction than another route. Accordingly, the described routes of administration are merely exemplary and are in no way limiting. 2DG (2-deoxyglucose) is currently in clinical trials for the treatment of solid tumors, and has been used in the treatment of herpes, HIV, SARS, influenza and hepatitis B which may also provide a secondary advantage in the prevention of clicially compromising viral infections. According to one aspect of the invention, it has been demonstrated that 2DG, a non-metabolizable analog of glucose, induces intra-cellular signals which cause ATF4 to bind to the master regulatory factor, FOXO3a, gene inducing its expression and thus activity preventing the maturation of primordial follicles. FOXO3a has been shown to block the maturation of follicles in oocytes, acting as a master regulator of ovulation. Additionally, FOXO3a has been strongly associated with an increased life span in a variety of organisms including humans. Mice completely lacking FOXO3a become infertile within a few weeks of birth because all ovarian follicles are activated due to the lack of the "FOXO3a brake." These traits are analogous to premature menopause or primary ovarian failure (POF) in humans. Furthermore, transgenic mice that specifically overexpress FOXO3a in the oocytes are unable to reproduce due to the constant presence of the FOXO3a brake and a lack of mature follicles available for ovulation, also leading to infertility.

In an aspect of the present invention, the approach is similar to that exhibited bu the overexpressing transgenic mice, in that treatment with 2DG increases FOXO3a mRNA and protein levels, which in turn is believed to prevent ovulation/folliculogenesis. Equally important, the simple removal of 2DG allows for the return to normal control of follicular development for future family planning. Results have been obtained showing that treatment of human ovarian carcinoma cells in culture or in mouse ovarian organ culture with 2DG causes a specific induction of FOXO3a mRNA and protein expression. Furthermore, preliminary dose response studies in mice injected with 2DG for only two weeks reveal that 2DG can cause a 2-4 fold increase in mRNA synthesis of FOXO3a in the ovary, accompanied by a 32-60% decrease in maturation of primary follicles.

As a simple derivative of glucose, 2DG is easily synthesized and/or obtainable. 2DG is a glycolytic inhibitor which has been used in a large number of animal metabolic and nutritional studies, as well as in a number of human nutritional and cancer studies/clinical trials with no documented side effects. The inventors have also identified two additional glycolytic inhibitors believed to act similarly to 2DG in affecting follicle development.

D-mannoheptulose is a nutraceutical with possible inherent anti-cancer activity, and is also effective in controlling obesity. The inventors have surmised that D-mannoheptulose induces FOXO3a synthesis in cell culture.

5-thio-D-glucose has been shown to prevent drug induced diabetes and is effective in causing reversible control of male fertility. The inventors have surmised that 2DG, D-mannoheptulose, and 5-thio-D-glucose, alone or in combination, can effectively block ovulation by inducing expression of FOXO3a. The inventors have therefore discovered a broadly acceptable, affordable and effective female contraceptive.

According to another embodiment, a derivative of 2DG, 2-deoxy-2-($^{18}$F)fluoro-D-glucose ($^{18}$F-FDG), a radiopharmaceutical is routinely used as a contrast agent in medical imaging using positron emission tomography (PET). This is based on the fact that cancer cells depend heavily on glucose as their prime energy source and therefore readily take up $^{18}$F-FDG which is thus easily detectable by PET. The $^{18}$F-FDG has a short half-life (109 minutes) and as such decays rapidly in the patients body to $^{18}$O-glucose-6-phosphate which is non-radioactive. This furthers demonstrates the utility of 2-DG and its derivatives in human exposure.

In one embodiment, the subject invention provides a non-hormonal female contraceptive composition comprising two or more of the following: (i) 2-deoxyglucose (2DG) or a combination of 2DG with chemical derivatives of 2DG with similarly documented ovarian activity; (ii) D-mannoheptulose; (iii) 5-thio-D-glucose; or an acceptable pharmaceutical salt thereof. It is noted that glucose and 2-DG are already freely soluble in aqueous solutions which provides a clear advantage for any formulation utilizing 2DG.

In another embodiment, the subject invention relates to a method for decreasing the fertility of a female subject, comprising administering a therapeutically effective amount of a glucose analog to the female subject, wherein the glucose analog comprises one or more of (i) 2-deoxyglucose (2DG) or a combination of 2DG with chemical derivatives of 2DG with similarly documented ovarian activity; (ii) D-mannoheptulose; or (iii) 5-thio-D-glucose; and the administering step inhibits ovulation in the female subject. In a further embodiment, the glucose analog elevates the production of FOXO3a.

Figure 2:
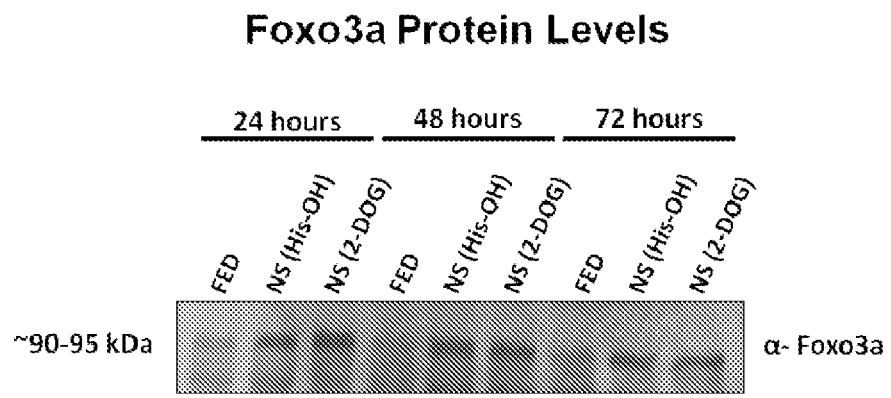
FIG. 2 provides an immunoblot analysis which shows Foxo3a protein levels are increased by 2-DOG, as well as by the amino acid mimetic histidinol, His-OH.

In yet a further embodiment, FOXO3a prevents activation of oocytes during follicle development. In another embodiment, a therapeutically effective amount of at least one glucose analog is co-administered to the female subject. In one example, FOXO3a mRNA and protein levels are induced in response to amino acid and glucose_deprivation in human ovarian carcinoma (SKOV3) cells. In order to establish a connection between FOXO3a and glucose deprivation, one example was used in which human ovarian carcinoma (SKOV3) cells were treated with 2-deoxyglucose (2-DOG or 2-DG) followed by mRNA analysis by real-time RT-PCR (FIG. 1) and immunoblot analysis (FIG. 2). 2-DG has been effectively employed as an alternative to glucose (deprivation) depletion. FIG. 1 demonstrates that Foxo3a mRNA is induced approximately 2.5 fold in response to 2-DOG treatment by 4 h, and that this induction is maintained out to 24 h. The fold increases were determined using a $\Delta\Delta CT$ method with cyclophilin A as the internal reference gene for each sample. FOXO3a protein levels are also increased by 2-DOG, as well as by the amino acid mimetic histidinol, His-OH, which is analogous to histidine or essential amino acid deprivation (FIG. 2). Control cells (FED/MEM) were given complete media.

Figure 3:
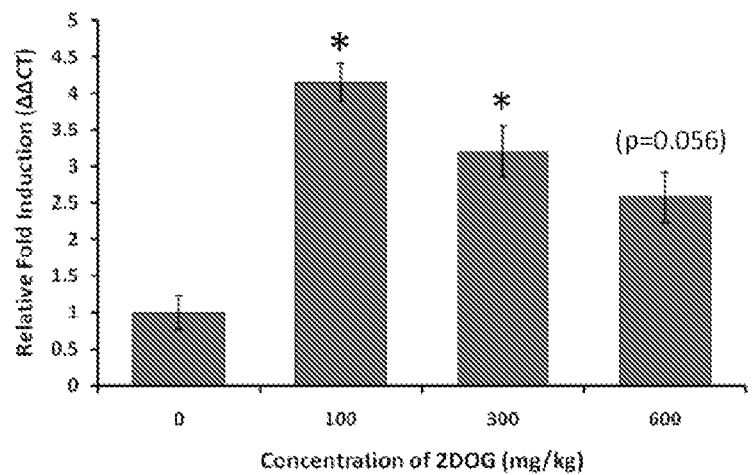
FIG. 3 provides a bar graph of real-time RT-PCR data showing a ~4 fold increase in Foxo3a levels.
Figure 4:
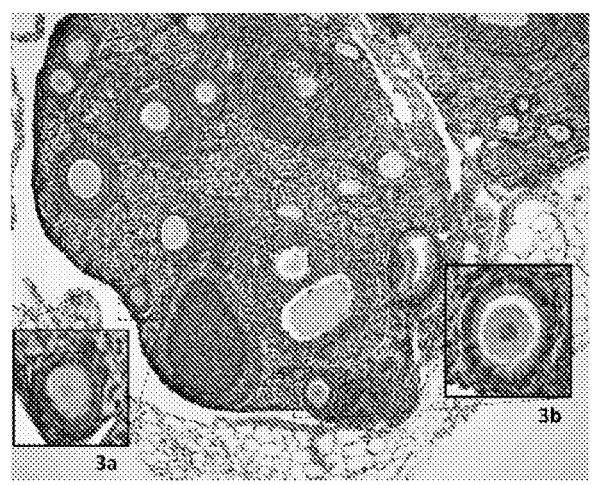
FIG. 4 provides a cross-sectional view showing follicles with one complete layer of <20 granulosa cells were identified as type 3a, while follicles with one complete layer of >20 granulosa cells were identified as type 3b.
Figure 5:
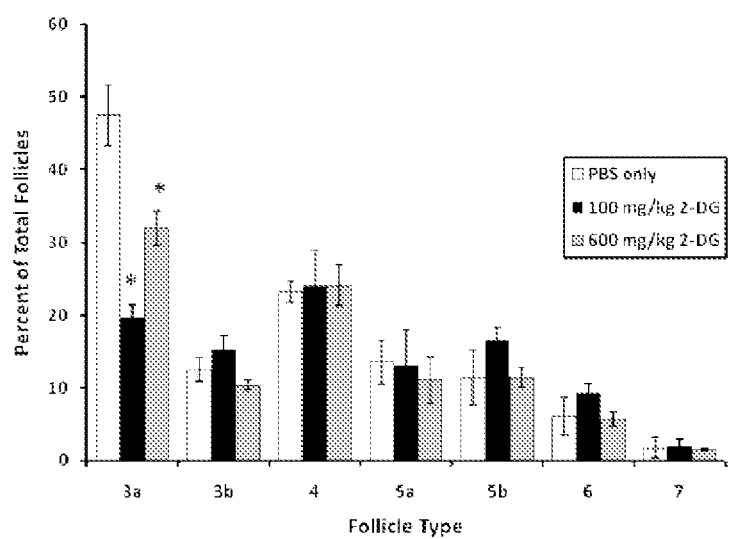
FIG. 5 provides a bar graph of collective data representing the total estimated number of each follicle type in each ovary following exposure to two concentrations of 2-DG. Results show that 2-DG at 100 mg/kg causes a ~60% reduction in type 3a follicles compared to PBS controls.

Not to be bound to any particular mechanism, it is believed that in one aspect of the present invention, by administering a therapeutically effective amount of the non-hormonal contraceptive composition to a female subject, cellular signals are induced activating a regulatory factor which blocks maturation of the follicles in the oocytes and suppresses ovulation. In one example, a pilot study was conducted in which 5-week-old mice were intraperitoneally (IP) injected daily with 2-DG for two weeks. To determine an effective dose, 100, 300 and 600 mg/kg 2-DG was tested, with 6 animals in each treated group and 6 mice in the control group (0) injected with PBS. Following the two week study, the mice were sacrificed and the ovaries removed for mRNA and histological analyses. FIG. 3 is a bar graph of real-time RT-PCR data with Foxo3a levels displaying a ~4 fold increase at 100 mg/kg 2-DOG and ~2.75 fold at 600 mg/kg 2-DOG level, illustrating a reverse dose response. The contralateral ovary was used for histological analysis of the total numbers of follicle types in the entire ovary. Ovaries were fixed in 10% neutral buffered formalin, embedded in paraffin, then serially sectioned at 8 μm and stained with hematoxylin. Follicles were counted in every fifth section with random start. Follicles were classified following Pedersen and Peters guidelines. Most relevant to the data presented here, type 3a and 3b follicles were classified as having a single layer of granulosa cells surrounding the oocyte, and the two were distinguished from each other by the number of granulosa cells in that single layer. As illustrated in FIG. 4, follicles with one complete layer of <20 granulosa cells were identified as type 3a, while follicles with one complete layer of >20 granulosa cells were identified as type 3b. Only follicles containing an oocyte with a clearly visible nucleus were scored, to ensure that each follicle was counted only once. It should be noted that type 3a follicles are the first stage of folliculogenesis from the primordial follicle, the dormant stage at which FOXO3a acts as a brake. After follicles were counted in each fifth section, the total number of each type was multiplied by a correction factor of five to estimate total number of follicles in each ovary. The collective data is shown in the bar graph in FIG. 5. The results demonstrate that the mice treated with either 100 mg/kg or 600 mg/kg 2-DG showed a statistically significant reduction in the number of type 3a follicles (60% and 32%, respectively). These data correlate with the mRNA levels shown in FIG. 3. Most significantly, these data demonstrate that the lower concentration (100 mg/kg) exhibited the most effective response (an inverse dose response), implying that even lower concentrations thresholds may be as effective. This is particularly advantageous as it allows lower dosages of one of the analogs or dosages of two or more analogs in therapeutic compositions. In a specific embodiment, the invention pertains to a composition that is dosed to provide a subject 250 mg/kg or less, 200 mg/kg or less, 150 mg/kg or less, or 100 mg/kg or less glucose analog such as 2DG, or derivatives thereof.

Figure 6:
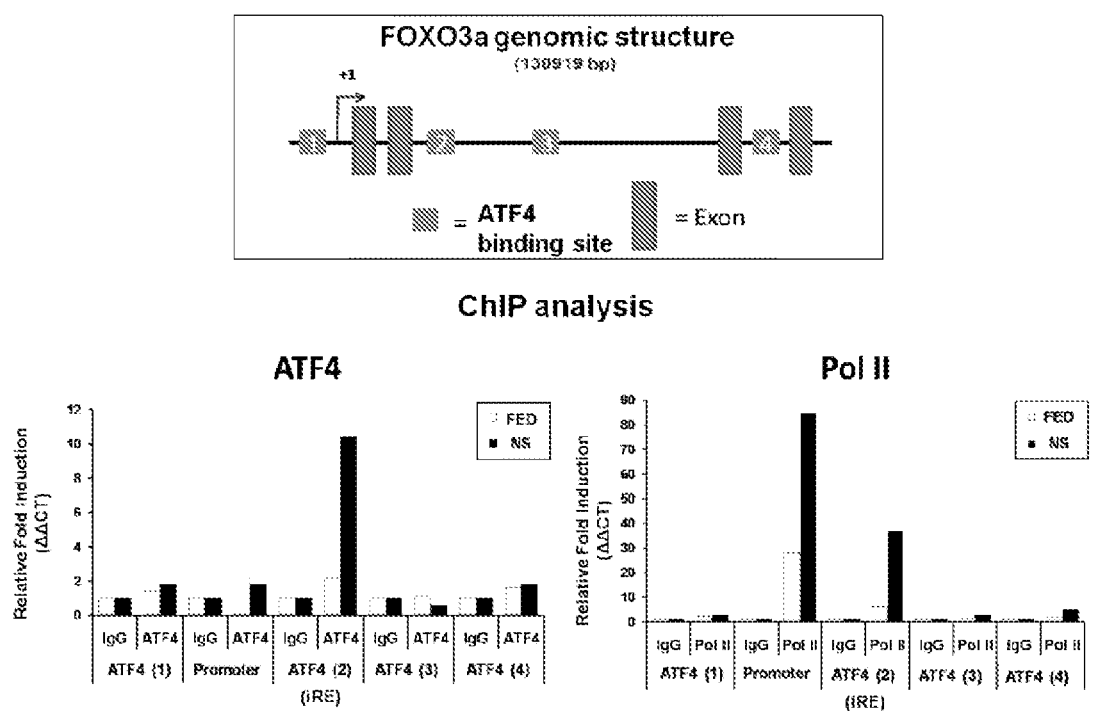
FIG. 6 shows a diagram of the Foxo3a gene and ChIP analysis showing that nutrient stress (NS) causes the inducible binding of the transcription factor ATF4, to a specific internal regulatory element (iRE) as well as inducible RNA polymerase II (Pol II) binding to the FOXO3 promoter and the iRE. of FIG. 7 shows results of studies conducted to determine affect of ATF4 knockdown on Foxo3a expression. ATF4 knockdown blocks the induction of FOXO3a mRNA and inhibits the binding of PolII to the iRE.

In another embodiment, it has been shown that ATF4 and Pol II inducibly bind to an internal ATF4 site within the Foxo3a gene by NS._ATF4 plays a major role in the regulation of many nutrient regulated genes. For example, Su et al. (19) completed a detailed characterization of an ATF4 binding site responsible for the NS regulation of the human asparagine synthetase gene. FIG. 6 (top) shows the human Foxo3a locus and the location of four potential ATF4 binding sites which contain perfect matches to the ATF4 consensus sequence: (G/A/C)TT(G/A/T)C(G/A)TCA (19). To evaluate ATF4 binding, ChIP analysis was used on SKOV3 cells placed in normal or NS conditions. As shown in FIG. 6 (bottom left), ATF4 interacts with a specific binding site (ATF4 (2)) within an intron of the Foxo3a gene which we have defined as an intronic regulatory element (iRE). It was observed that inducible binding of ATF4 to only one out of four in silico defined sites in proximity to the gene. These results led to the hypothesis that this iRE may be an important regulatory element for Foxo3a. Pol II binding under the same conditions was also evaluated. FIG. 3 (bottom right) demonstrates that Pol II binds inducibly to the promoter as well as to the iRE, thus providing evidence for the potential interaction between the promoter and the iRE. These studies demonstrate that ATF4 and Pol II bind to the iRE of the Foxo3a gene led to the development of a reporter assay to determine if this site was transcriptionally functional. A ~100 bp fragment containing the iRE was subcloned into a human growth hormone (hGH) reporter vector driven by the minimal viral thymidine kinase (TK) promoter. Transfection of this construct in NS conditions caused a 12-14 fold increase over control, demonstrating the functional significance of this regulatory region (data not shown).

Figure 7:
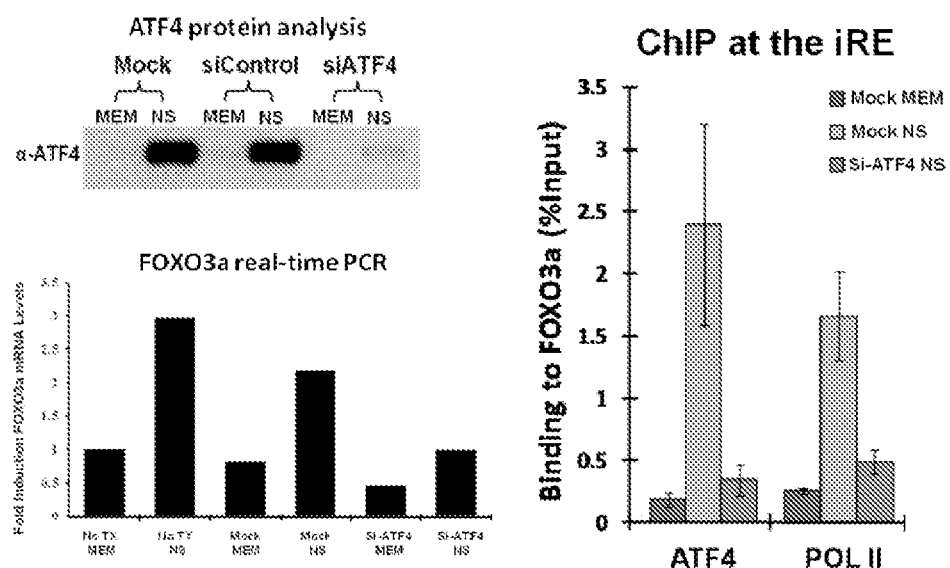

ATF4 regulates mRNA induction of Foxo3a as well as recruitment of Pol II to the iRE. To determine if ATF4 plays a functional role in the NS induction of Foxo3a, human liver hepatoma (HepG2) cells were treated with a mixture of four ATF4 siRNAs. FIG. 7 (top left) demonstrates the effective knockdown of ATF4 protein by siRNA. To determine the role of ATF4 in Foxo3a mRNA induction, cells were transfected with the indicated siRNA and placed in NS conditions or control (MEM) conditions. After 12 h of treatment, the total RNA was isolated and Foxo3a mRNA levels were determined by real-time RT-PCR. FIG. 7 (bottom left) illustrates the real-time RT-PCR analysis of Foxo3a mRNA levels, demonstrating that knockdown of ATF4 reduces the induction of Foxo3a by NS. It was next hypothesized whether ATF4 plays a role in Pol II recruitment, then knockdown of ATF4 by siRNA should also block the recruitment of Pol II to the iRE. As expected, the presence of ATF4 siRNA results in a significant reduction in induced ATF4 binding to the iRE by ChIP (FIG. 4, right). Most significantly, it was also observed that ATF4 siRNA inhibited the inducible binding of Pol II to the iRE.

These data implicate a role for the ATF4 in the mediation of Foxo3a gene expression, thus forming the basis for studies to evaluate this novel connection between Foxo3a and ATF4 and establishing the rationale for addressing a potential role for ATF4 in ovarian biology.

In another embodiment, there is provided a method of preserving the supply of oocytes in a female subject, comprising administering a non-hormonal composition to a female subject. The composition includes 2-deoxyglucose (2DG) or a combination of 2DG with chemical derivatives of 2DG with similarly documented ovarian activity one or more of (i) 2-deoxyglucose (2DG); (ii) D-mannoheptulose; or (iii) 5-thio-D-glucose, wherein the administration halts ovulation thus preserving the female reserve of oocytes. Specifically, oocytes are prevented from undergoing activation and maturation during each normal menstrual cycle thus preserving a larger population of oocytes, "ovarian reserve", over the child bearing age of the female.

In a further embodiment, the inhibition of ovulation may also provide the added positive effect of preserving female ovarian reserve leading to the effect of delaying onset of menopause. The composition includes 2-deoxyglucose (2DG) or a combination of 2DG with chemical derivatives of 2DG with similarly documented ovarian activity wherein the administration halts ovulation.

In a further embodiment, there is provided a method of inhibiting ovulation. The method comprises administering to a female subject a composition, comprising one or more of the following: (i) 2-deoxyglucose (2DG); (ii) D-mannoheptulose; or (iii) 5-thio-D-glucose.

In yet another embodiment, there is provided a method for decreasing the fertility of a female subject, comprising administering at least one unit dose of a compound comprising 2-deoxyglucose (2DG) or a combination of 2DG with chemical derivatives of 2DG with similarly documented ovarian activity one or more of (i) 2-deoxyglucose (2DG); (ii) D-mannoheptulose; or (iii) 5-thio-D-glucose to the female subject, every other day, for a period of 4 weeks. In an alternative embodiment the compound is administered to the female subject for a period of 6 weeks. In yet another alternative embodiment, the compound is administered to the female subject for a period of 3 months. In an alternative embodiment the compound is administered to the female subject for a period of 12 months.

In one embodiment, the compound is administered to the female subject once daily. In an alternative embodiment, the compound is administered to the female subject twice daily.

In another aspect, a contraceptive system for at-home use is provided. The system includes a kit, including at least one container, wherein the container comprises 2-deoxyglucose (2DG) or a combination of 2DG with chemical derivatives of 2DG with similarly documented ovarian activity or other glucose compounds. The other glucose compounds include: D-mannoheptulose; and 5-thio-D-glucose. The glucose compounds are combined in a predetermined manner and a therapeutically effective amount to decrease fertility in a female subject. In another embodiment, the system includes multiple containers, wherein each compound is housed in an individual and separate container.

Dosage

The dose administered to an animal, particularly a human, in accordance with the present invention should be sufficient to effect the desired response in the animal over a reasonable time frame. One skilled in the art will recognize that dosage will depend upon a variety of factors, including the strength of the particular compositions employed, the age, species, condition, and body weight of the animal. The size of the dose also will be determined by the route, timing and frequency of administration as well as the existence, nature, and extent of any adverse side effects that might accompany the administration of a particular composition and the desired physiological effect. It will be appreciated by one of ordinary skill in the art that various conditions or desired results, may require prolonged treatment involving multiple administrations.

Suitable doses and dosage regimens can be determined by conventional range-finding techniques such as pharmaceutical dose response curves known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of at least 2-deoxyglucose (2DG) or possibly in combination with 2DG chemical derivatives with similar activity; optionally in combination with (ii) D-mannoheptulose; or (iii) 5-thio-D-glucose, in a dosage amount of from about 0.1 mg/kg/day to about 100 mg/kg/day, preferably from about 0.1 mg/kg/day to about 100 mg/kg/day, if administered systemically. A preferred concentration for topical administration is 100 mu·M.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the compound, the route of administration, pharmacological considerations such as the activity, efficacy, pharmacokinetics and toxicology profiles of the compound and any secondary agents being administered, and the like. Patients undergoing such treatment will typically be monitored on a routine basis to determine the effectiveness of therapy. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of compound that exhibits the desired effectiveness is administered and, further, that administration is continued only so long as is necessary to successfully achieve the optimum effect.

Pharmaceutical Compositions

Various embodiments of the invention are foreseen to have valuable application as constituents of pharmaceutical preparations to treat various conditions generally defined as pathologies. Accordingly, embodiments of the invention also comprise pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, intra-vaginal administration similar to the nuvaring product (http://www.nuvaring.com/Consumer/index.asp) which this involves a monthly treatment with slow release of the active agent, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof.

When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. The compositions may be contained in a vial, sponge, syringe, tube, or other suitable container. The inventor points out that since glucose is normally considered to not decompose in the stomach but rather is readily uptaken by glucose transporters in the small intestine this provides an advantage over other compounds that are denatured or whose chemical bonds are broken in the intestine.

As used herein, the term "effective amount" refers to the amount of a therapy that is sufficient to result in the suppression of ovulation, the inhibition of or reduction of fertility in a female subject, and the preservation of oocyte reserve, as well as delaying menopause.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human of the female gender.

As used herein, the term "administering" or "administration" includes but is not limited to oral or intravenous administration by liquid, capsule, tablet, spray or intravaginal. Administration may be by injection, whether intramuscular, intravenous, intraperitoneal or by any parenteral route. Parenteral administration can be by bolus injection or by continuous infusion. Formulations for injection may be presented in unit dosage form, for example, in ampoules or in multi-dose containers with an added preservative. The compositions may take the form of suspensions, solutions or emulsions in oily or aqueous vehicles and may contain formulatory agents such as suspending, stabilizing and/or dispersing agents. Alternatively the compositions may be in powder form (e.g., lyophilized) for constitution with a suitable vehicle, for example sterile pyrogen-free water, before use. Compositions may be delivered to a female subject by inhalation by any presently known suitable technique including a pressurized aerosol spray, where the dosage unit may be controlled using a valve to deliver a metered amount.

In another specific embodiment, the invention pertains to an apparatus having a glucose analog such as 2DG or 2DG derivatives loaded thereon that can be positioned the vagina of a patient such that the glucose analog is released over a period time in a controlled manner. The apparatus can take a configuration similar to the nuvaring product whereby glucose analog is released over a period of time such over the course of a month.

Administration by capsule and cartridges containing powder mix of the composition can be used in an inhaler or insufflator to deliver the particles to the female subject. Still other routes of administration which may be used include buccal, urethral, vaginal, or rectal administration, topical administration in a cream, lotion, salve, emulsion, or other fluid may also be used.

The term "co-administration" or "co-administering" as used herein refer to the administration of a substance before, concurrently, or after the administration of another substance such that the biological effects of either substance synergistically overlap.

It is noted that the term "pharmaceutically acceptable salt(s)" refers to salts derived from treating a compound of the composition with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similarly known acceptable acids.

"Container" as used herein refers to a housing for a compound or composition, and includes but is not limited to: capsules, tablets, ampoules, aerosol cans, sponges, syringes, vials, tubes, bottles, pouches, intravaginal rings and strips.

The disclosures of any references cited herein is incorporated in their entirety to the extent not inconsistent with the teachings herein.

What is claimed is:

1. A method for decreasing the fertility of a female subject in need thereof comprising administering a therapeutically effective amount of a glucose analog composition to said female subject, wherein said glucose analog composition comprises:
   a) 2-deoxyglucose (2DG) or a pharmaceutically acceptable salt thereof or a combination of said 2DG with one or more chemical derivatives of 2DG
   b) optionally D-mannoheptulose or a pharmaceutically acceptable salt thereof; and
   c) optionally 5-thio-D-glucose or a pharmaceutically acceptable salt thereof;
wherein said composition inhibits ovulation in said female subject.

2. The method of claim 1, wherein said glucose analog or chemical derivative thereof elevates the production of FOXO3a.

3. The method of claim 1, wherein said FOXO3a prevents activation of oocytes during follicle maturation.

4. The method of claim 1, wherein said glucose analog composition comprises a therapeutically effective amount of at least one chemical derivative of 2DG.

5. A method of inhibiting ovulation by administering to a female subject a composition according to claim 1.

6. The method of claim 5, wherein said composition is administered to said female subject for a period of at least 6 weeks.

7. The method of claim 5, wherein said composition is administered to said female subject for a period of at least 3 months.

8. The method of claim 5, wherein said composition is administered to said female subject once daily.

9. The method of claim 5, wherein said composition is administered to said female subject twice daily.

* * * * *